(12) United States Patent
Abel et al.

(10) Patent No.: US 7,781,597 B2
(45) Date of Patent: *Aug. 24, 2010

(54) PROCESS FOR THE SYNTHESIS OF ORGANIC COMPOUNDS

(75) Inventors: Stephan Abel, Weil am Rhein (DE);
Murat Acemoglu, Basel (CH);
Bernhard Erb, Gipf-Oberfrick (CH);
Christoph Krell, Basel (CH); Joseph Sclafani, Ledgewood, NJ (US); Mark Meisenbach, Durmenach (FR); Mahavir Prashad, Montville, NJ (US);
Wen-Chung Shieh, Berkeley Heights, NJ (US); Song Xue, Parsippany, NJ (US)

(73) Assignee: Novartis AG, Basel (CH)

( * ) Notice: Subject to any disclaimer, the term of this patent is extended or adjusted under 35 U.S.C. 154(b) by 91 days.

This patent is subject to a terminal disclaimer.

(21) Appl. No.: 11/915,691

(22) PCT Filed: Jun. 7, 2006

(86) PCT No.: PCT/US2006/022154

§ 371 (c)(1),
(2), (4) Date: Nov. 27, 2007

(87) PCT Pub. No.: WO2006/135640

PCT Pub. Date: Dec. 21, 2006

(65) Prior Publication Data

US 2008/0200692 A1    Aug. 21, 2008

Related U.S. Application Data

(60) Provisional application No. 60/688,976, filed on Jun. 9, 2005.

(51) Int. Cl.
C07D 233/56    (2006.01)
(52) U.S. Cl. .................................... 548/343.5
(58) Field of Classification Search ............... 548/343.5, 548/341.5, 335.5
See application file for complete search history.

(56) References Cited

U.S. PATENT DOCUMENTS 4,728,653 A * 3/1988 Campbell et al. ............ 514/312
2008/0200691 A1 * 8/2008 Acemoglu et al. ......... 548/335.5
2008/0312251 A1   12/2008 Sun et al.

FOREIGN PATENT DOCUMENTS

| EP | 0166533 | 1/1986 |
| WO | WO 01/53274 | 7/2001 |
| WO | WO 03/099771 | 12/2003 |
| WO | WO 2004/005281 | 1/2004 |
| WO | WO 2004/029038 | 4/2004 |

OTHER PUBLICATIONS

Sun et al., "Preparation of pyrimidine derivatives as protein kinase inhibitors," Database accession No. 2006:655649 Abstract.
Tokunaga, Teruhisa, et al. "Oxindole derivatives as orally active potent growth hormone secretagogues", J. Med. Chem. vol. 44, pp. 4641-4649 (2001).

* cited by examiner

Primary Examiner—Kamal A Saeed
Assistant Examiner—Kristin Bianchi
(74) Attorney, Agent, or Firm—Sandra S. Shim

(57) ABSTRACT

The present invention provides an efficient, safe and cost effective way to prepare 5-(4-methyl-1H-imidazol-1-yl)-3-(trifluoromethyl)-benzenamine which is a key intermediate for the preparation of substituted pyrimidinylaminobenzamides of formula (II):

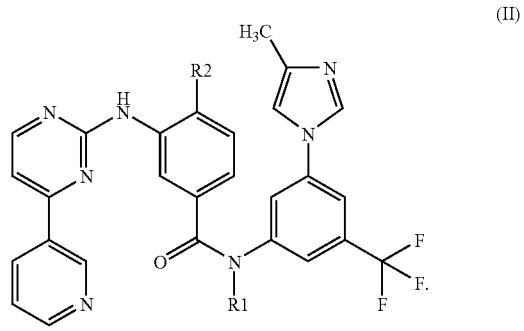

13 Claims, No Drawings

PROCESS FOR THE SYNTHESIS OF ORGANIC COMPOUNDS

This application claims benefit of U.S. Provisional Application No. 60/688,976, filed Jun. 9, 2005.

BACKGROUND OF THE INVENTION

The present invention provides an efficient, safe and cost effective way to prepare 5-(4-methyl-1H-imidazol-1-yl)-3-(trifluoromethyl)-benzenamine of the following formula (I):

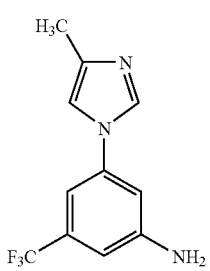
(I)

which is an intermediate for the preparation of substituted pyrimidinylaminobenzamides of formula (II):

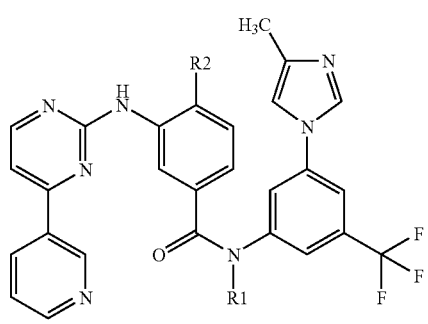
(II)

Compounds of formula (II) have been disclosed in W. Breitenstein et al, WO 04/005281 A1, the disclosure of which is incorporated herein by reference. These compounds have been shown to inhibit one or more tyrosine kinases, such as c-Abl, Bcr-Abl, the receptor tyrosine kinases PDGF-R, Flt3, VEGF-R, EGF-R and c-Kit. As such, compounds of formula (II) can be used for the treatment of certain neoplastic diseases, such as leukemia.

Previous synthesis of compound (I) involves a 4 step synthetic route starting with an aromatic substitution reaction of compound (III) with compound (IV), which requires employing high energy (150° C.) (Scheme 1).

Scheme 1

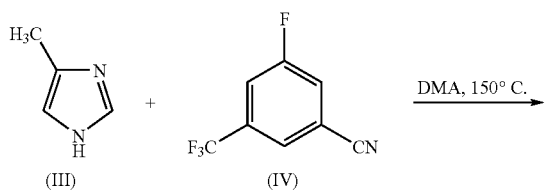

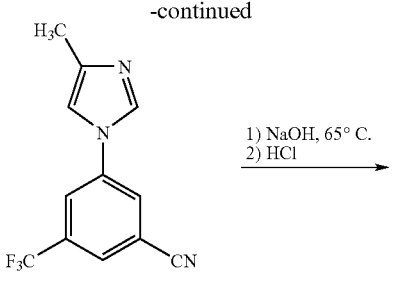
(V)

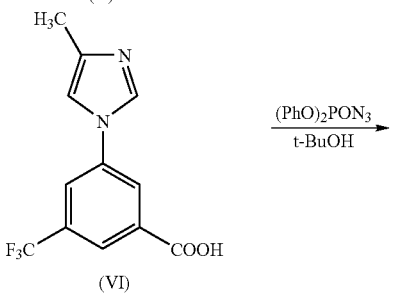
(VI)

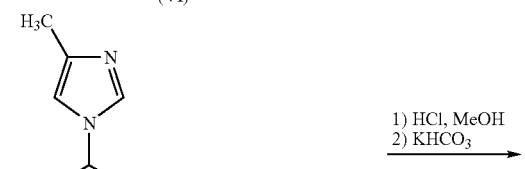
(VII)

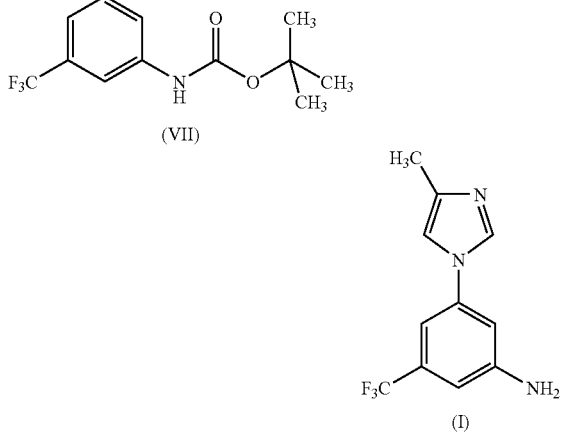
(I)

Furthermore, transformation of compound (VI) to compound (VII) via Curtius rearrangement utilizes an unsafe reagent, diphenylphosphorylazide. This reaction produces inconsistent product yields and quality, and removal of the resulting diphenylphosphoric acid by-product is difficult. The carbamate product (VII) needs to be purified by chromatography, which is expensive and time consuming for commercial operations.

It is an object of this invention to provide alternative processes to make the compound of formula (I) efficiently and in high yields.

It is a further object of this invention to make compound (I) from lower cost starting materials and reagents.

It is a still further object of this invention to provide for a process to make the compound of formula (I) using safer reagents.

It is further objective to use a faster heating and cooling cycle or shorter reaction time intervals, e.g., using microwave fields or by additional heat exchanger capacity in batch vessels or by using continuous reaction equipment will lead to less decomposition and cleaner reaction.

The present invention overcomes the problems of the reaction shown in Scheme 1 above.

The present invention also includes a novel intermediate compound (XVIII), and its preparation.

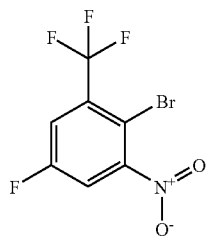

(XVIII)

SUMMARY OF THE INVENTION

The present invention provides novel synthetic processes for the manufacture of 5-(4-methyl-1H-imidazol-1-yl)-3-(trifluoromethyl)-benzenamine having formula (I):

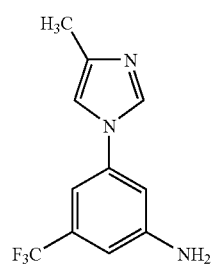

(I)

The compound of formula (I) is an intermediate for the preparation of substituted pyrimidinylamino-benzamides of formula (II):

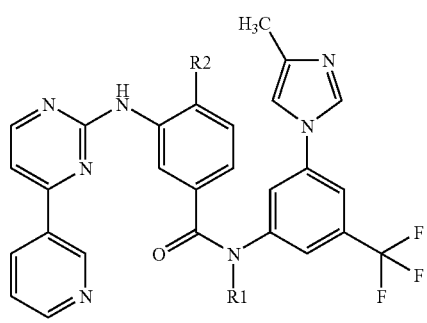

(II)

The compounds of formula (II) have been disclosed in W. Breitenstein et al., WO 04/005281, which published on Jan. 15, 2004, the disclosure of which is incorporated by reference. A preferred compound of formula (II) is 4-methyl-3-[[4-(3-pyridinyl)-2-pyrimidinyl]amino]-N-[5-(4-methyl-1H-imidazol-1-yl)-3-(trifluoromethyl)phenyl]benzamide. Compounds of formula (II) can be used for the treatment of certain neoplastic diseases, such as leukemia.

More specifically, the present invention provides the general process of making compound (I) as follows:

Scheme 2

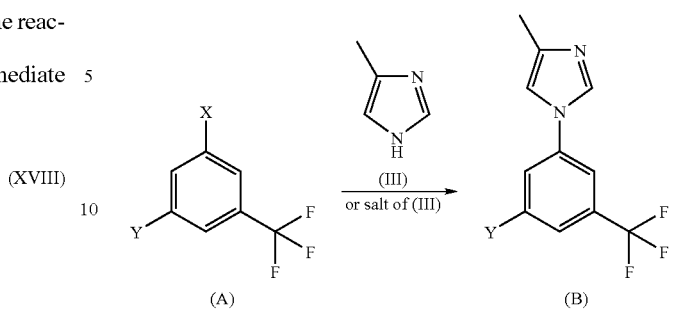

wherein
X is halogen, sulfonate or $NO_2$; and
Y is $NH_2$, $NO_2$, halogen or CN.

The general reaction scheme is to react (A) and (III) under suitable reaction conditions to prepare (B). When Y is $NH_2$, then (B) is the compound of formula (I). When Y is $NO_2$ or CN, or X and Y are both halogens, additional process steps are needed, as set forth below.

DETAILED DESCRIPTION OF THE INVENTION

The general reaction scheme of the invention can be illustrated in the following embodiments:

The first embodiment is represented by reaction Scheme 3:

Scheme 3

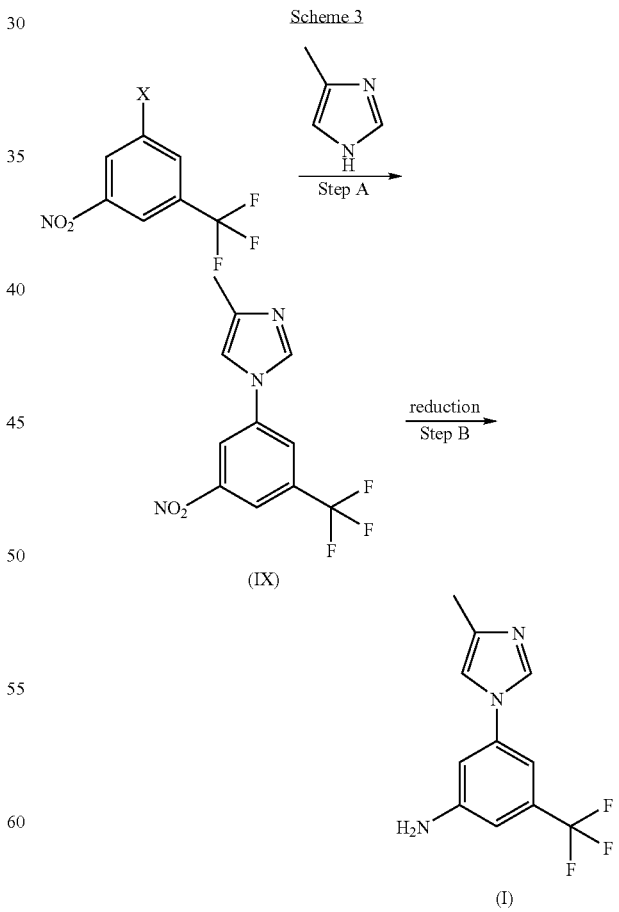

where Y in compound A is $NO_2$:
Here, X can be halogen, sulfonate or $NO_2$.

When X is Br, Step A comprises the use of a transition metal catalyst and a mild to strong base, and Step B comprises a reduction step using a transition metal catalyst in a suitable polar solvent.

When X is hydrogen, the reaction is modified by Scheme 4:

Scheme 4

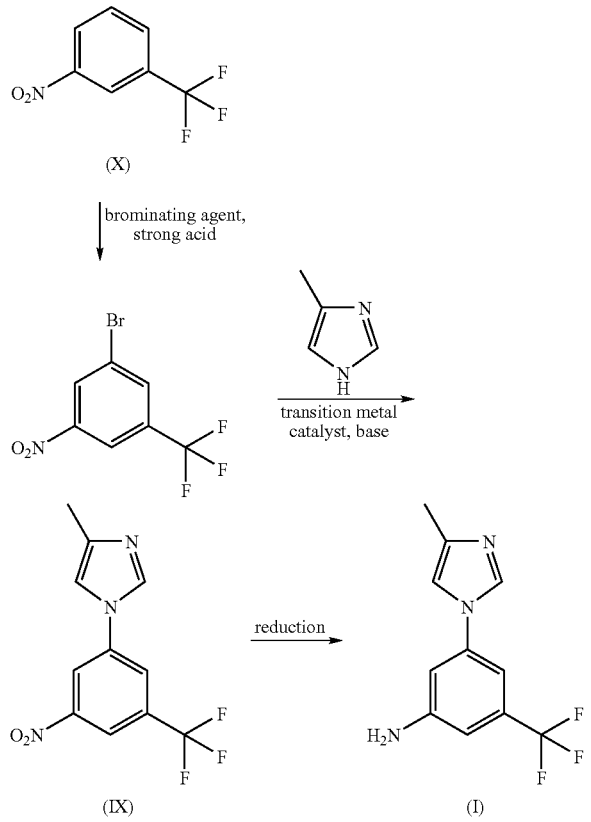

This process comprises:
(i) treating 1-nitro-3-trifluoro-methyl-benzene (X) with a brominating agent, preferably with 1,3-dibromo-5,5-dimethylhydantoin (i.e., 1,3-dibromo-5,5-dimethyl-imidazolidine-2,4-dione), in the presence of a strong acid, preferably concentrated sulfuric acid, in an inert solvent, preferably dichloromethane, at a temperature of 25-40° C., preferably 35° C., to give 1-bromo-3-nitro-5-trifluoro-methyl-benzene (XI) as main product,
(ii) reacting a mixture of 1-bromo-3-nitro-5-trifluorom-ethyl-benzene (XI) and 4-methyl-1H-imidazole in the presence of a transition metal catalyst, such as a copper, palladium or nickel compound, preferably a copper(I) salt, and a moderately strong to mild base, preferably a carbonate, alkanoate or hydrogencarbonate salt, and optionally a coordinating additive, such as a 1,2-di-amine, preferably ethylene-diamine, in a dipolar aprotic solvent, preferably N,N-dimethylformamide or 1-methyl-2-pyrrolidinone, at elevated temperature, preferably at 100-120° C., to give 4-methyl-1-(3-nitro-5-trifluoromethyl-phenyl)-1H-imidazole (IX) as the main product,
(iii) reducing 4-methyl-1-(3-nitro-5-trifluoromethyl-phenyl)-1H-imidazole (IX), preferably using hydrogen in the presence of a transition metal catalyst, in a polar solvent, preferably methanol or ethanol, and, preferably at elevated temperature to give 5-(4-methyl-1H-imidazol-1-yl)-3-(trifluoromethyl)-benzenamine (I). Starting materials 1-Nitro-3-trifluoromethyl-benzene (X) and 4-methyl-1H-imidazole are commercially-available.

When X is iodine, Scheme 3 above, Step A comprises the use of a transition metal catalyst and a mild to strong base, and Step B comprises a reduction step using a transition metal catalyst in a suitable polar solvent as shown below in Scheme 5:

Scheme 5

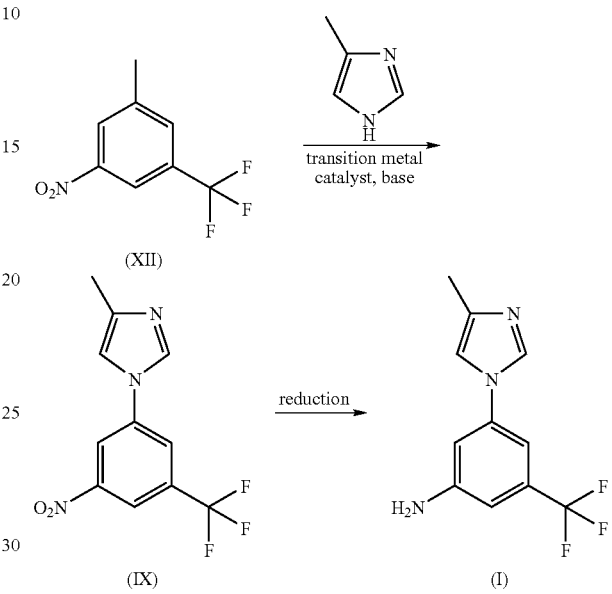

Compound (I) can be prepared starting from 1-iodo-3-nitro-5-trifluoromethyl-benzene (XII) using the methodology of steps (ii) and (iii) described above. The preparation of 1-iodo-3-nitro-5-trifluoromethyl-benzene (XII) is described in *J Med Chem*, Vol. 44, p. 4641 (2001).

When X is F, in Scheme 3 above, Step A comprises the use of a strong to mild base in a solvent at an elevated temperature (70-130° C.) and Step B comprises a reduction step using a transition metal catalyst in a suitable polar solvent as shown below:

Scheme 6

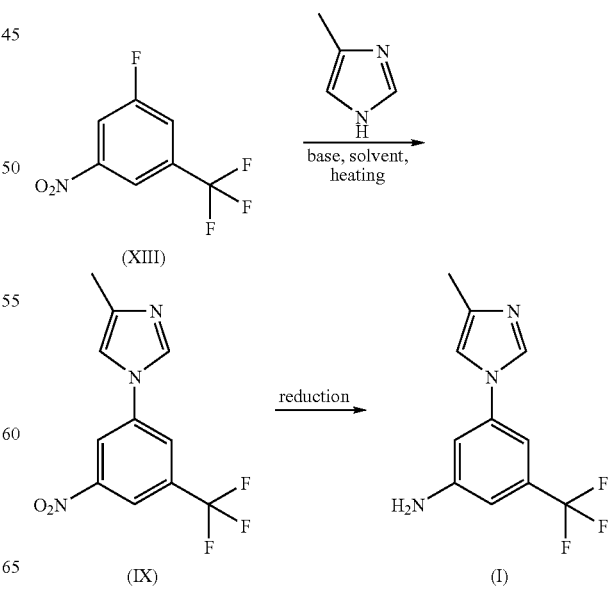

This process comprises:

(i) reacting a mixture of 1-fluoro-3-nitro-5-trifluoro-methyl-benzene (XIII) and 4-methyl-1H-imidazole in the presence of a moderately strong to mild base, preferably a carbonate or hydrogencarbonate salt, in a suitable solvent, preferably N,N-dimethylformamide, N,N-dimethylacetamide or 1-methyl-2-pyrrolidinone, at 70-130° C., preferably at 75-100° C., to give 4-methyl-1-(3-nitro-5-trifluoromethyl-phenyl)-1H-imidazole (IX) as the main product; and (ii) reducing 4-methyl-1-(3-nitro-5-trifluoromethyl-phenyl)-1H-imidazole (IX), preferably using hydrogen in the presence of a transition metal catalyst, in a suitable polar solvent, preferably methanol or ethanol, and, preferably at an elevated temperature to give 5-(4-methyl-1H-imidazol-1-yl)-3-(trifluoromethyl)-benzenamine (I). This embodiment can also be a coupling reaction.

In addition, each of the processes described above may optionally involve the transformation of compound (IX) into a salt of the formula (XV), e.g., for purification reasons, as illustrated by the following scheme:

Scheme 7

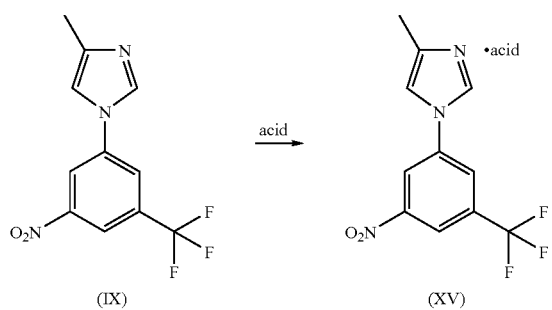

(IX)                    (XV)

Here, a solution of compound (IX) is treated with an acid, or a solution thereof in water or an organic solvent, followed by isolation of the salt (XV), e.g., by filtration. Compound (IX) may then be obtained by treating salt (XV) with a base, preferably with aqueous sodium hydroxide solution, and isolating the free base (IX) by extraction or crystallization.

For the first embodiment, the strong to mild base is preferably a carbonate, alkonate or hydrogencarbonate; more preferably potassium alkoxide, sodium alkoxide, lithium alkoxide, potassium hydride, sodium hydride, or a carbonate of lithium, sodium, potassium or cesium.

A second embodiment of Scheme 2 is when Y is $NH_2$. Here a first sub-embodiment is when X is halogen. Where X is Br, the reaction is represented by Scheme 8:

Scheme 8

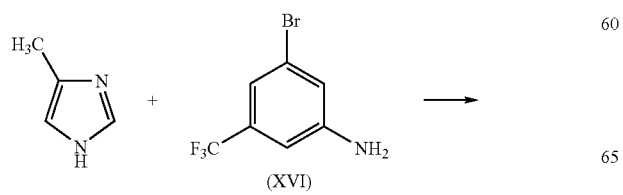

(XVI)

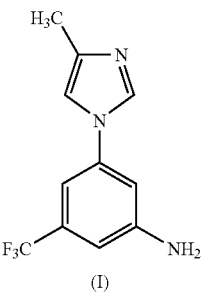

(I)

This reaction involves reacting a mixture of 3-bromo-5-trifluoromethyl-phenylamine (XVI) and 4-methyl-1H-imidazole in the presence of a transition metal catalyst, such as a copper, palladium or nickel compound, preferably a copper(I) salt, and a strong to mild base, preferably a carbonate, alkanoate or hydrogencarbonate salt, and optionally a coordinating additive, such as a 1,2-diamine, preferably cyclohexanediamine, in a dipolar aprotic solvent, preferably diglyme, N,N-dimethylformamide or 1-methyl-2-pyrrolidinone, at elevated temperature, preferably at 100-150° C., to give 5-(4-methyl-1H-imidazol-1-yl)-3-(trifluoromethyl)-benzenamine (I) as the main product.

When X is F, an alternative synthesis of (XIX) and (I) is provided utilizing inexpensive starting material 2-bromo-5-fluoro-benzotrifluoride (XVII). Therefore, a compound of formula (I) can be synthesized by the following scheme:

Scheme 9

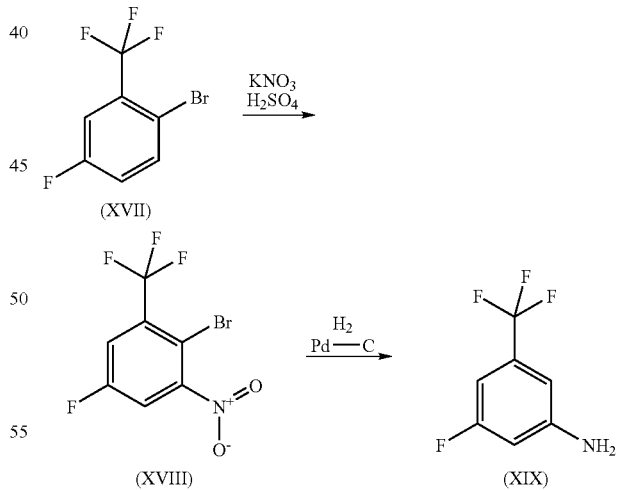

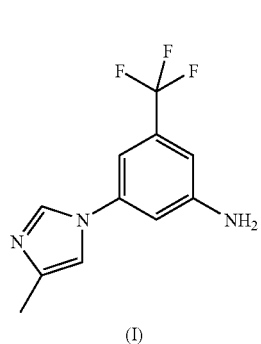

(I)

Nitration of the commercially readily available 2-bromo-5-fluoro-benzotrifluoride (XVII) with potassium nitrate and sulphuric acid gives the novel compound 2-bromo-5-fluoro-1-nitro-3-trifluoro-methyl-benzene (XVIII). Reduction of compound (XVIII) by catalytic hydrogenation on palladium/charcoal affords 3-fluoro-5-trifluoromethyl-phenylamine [compound (XIX)], which is reacted with the sodium salt of 4-methyl-imidazole to produce compound (I). Crude compound (I) comprises the desired product as the main product and at least one regioisomer as a by-product. Crude compound (I) can be recrystallized from toluene and renders pure compound (I) with >99.8 area % purity using HPLC.

It is noteworthy to mention that 3-fluoro-5-trifluoromethyl-phenylamine (XIX) is also commercially available in small quantities, e.g., from ABCR. The synthesis route described herein provides a new synthetic route to make compound (XIX) from the novel versatile compound (XVIII). 3-Fluoro-5-trifluoromethyl-phenylamine (XIX) prepared by this route proved to be identical with a commercially purchased sample from ABCR (ABCR F01075).

The novel compound (XVIII) disclosed herein is a versatile compound and can be used as a starting material for the synthesis of a variety of interesting trifluoromethyl-benzene derivatives, which are intermediates for the preparation of substituted pyrimidinylaminobenzamides of formula (II) which have been shown to have anti-leukemic activities. See WO 04/005281.

A third embodiment of Scheme 2 is when X is F and Y is CN. The reaction, by Hofmann Degradation, is represented by Scheme 10 below:

Scheme 10

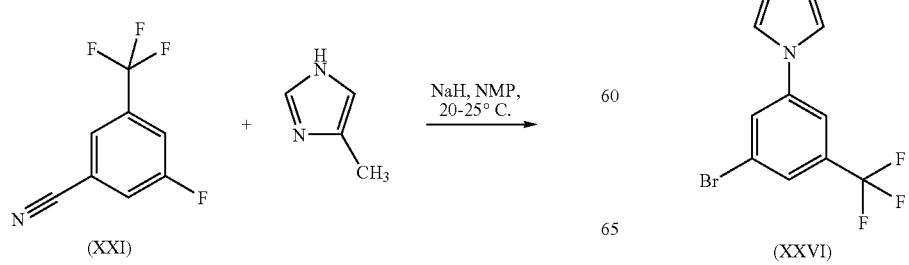

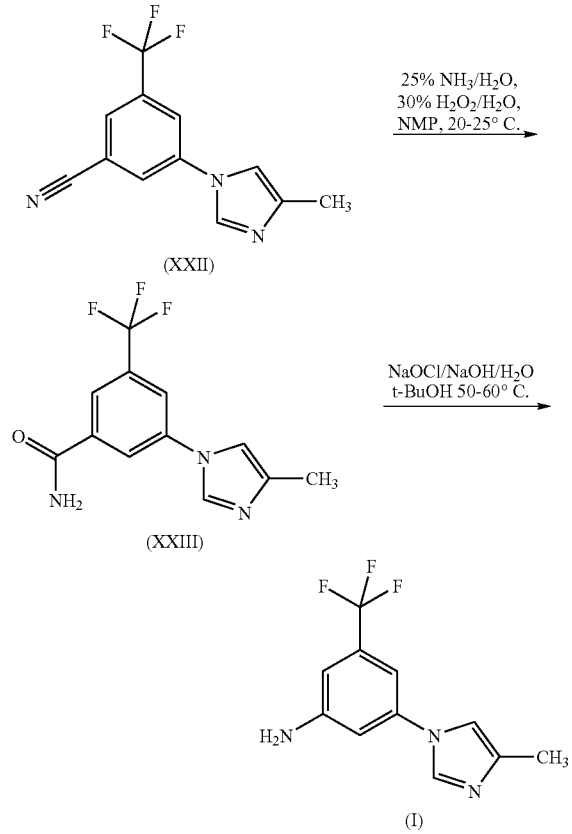

A fourth embodiment of Scheme 2 both X and Y are both halogens. This reaction is represented by the following scheme:

Scheme 11

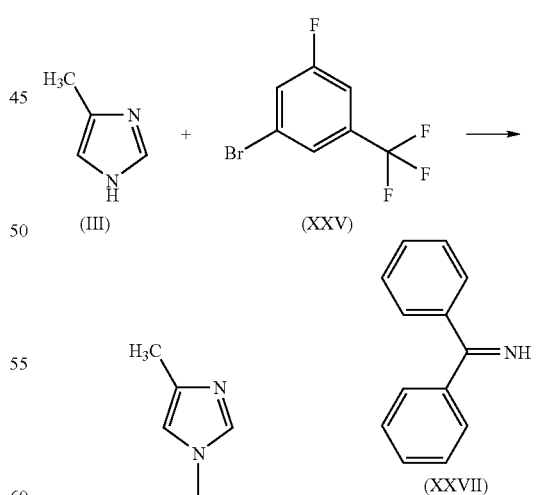

-continued

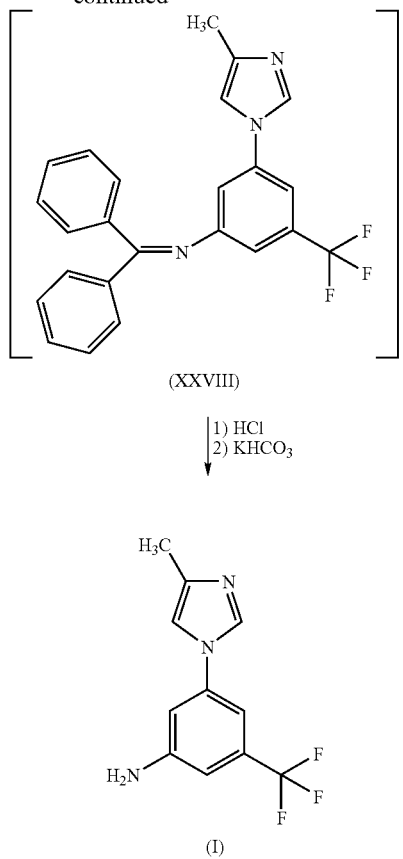

According to this process commercially-available 3-bromo-5-fluoro-benzotrifluoride (XXV) is reacted with 4-methylimidazole (III) at 25° C. in the presence of a strong base, such as NaH, thus generating crude compound (XXVI) [containing 16% regioisomer]. Crude compound (XXVI) can be recrystallized from heptane and renders pure bromoarene (XXVI) with no detectable amount of regioisomer. Arylamination of compound (XXVI) and diphenylimine (XXVII) in the presence of a palladium catalyst, a phosphine ligand, and a base, such as the combination of Pd(OAc)$_2$/Xantphos/NaO$^t$Bu or Pd(OAc)$_2$/BINAP/NaOtBu, yields imine (XXVIII). Residual palladium contents in compound (XXVIII) can be reduced to 3.4 ppm after PICA charcoal treatments. Hydrolysis of compound (XXVIII) with aqueous hydrochloric solution produces compound (I) in the form of the HCl salt. The salt can be converted to its free base [compound (I)] with potassium bicarbonate and thus affords pure compound (I) of high quality: HPLC purity >99%; palladium content 0.5 ppm. The process of the present invention is safer, more practical, and commercially acceptable than the previously utilized synthetic pathway (Scheme 1). Other palladium catalyst useful in the above reaction include tetrakis(triphenyl) phosphine palladium (0); tris(dibenzylideneacetone dipalladium (0) or palladium chloride, and other catalysts known to one of skill in the art. Other ligands useful in the above reaction include triphenylphosphine or trialkyl phosphines.

The following examples more particularly illustrate the present invention, but do not limit the invention in any way.

EXAMPLE 1

Synthesis of 1-[3-Bromo-5-(trifluoromethyl)phenyl]-4-methyl-1H-imidazole (XXVI)

Scheme 12

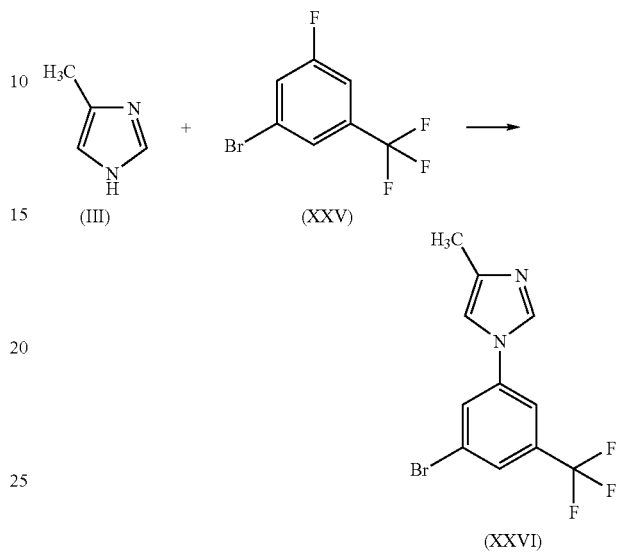

A 2 L, 4-neck, round-bottom flask equipped with a mechanical stirrer, a digital thermometer, heating/cooling capacity, an addition funnel, and a nitrogen inlet/outlet is charged 1-methyl-2-pyrrolidinone (113 g) and sodium hydride (8.0 g, 60% in oil) under nitrogen purge. The mixture is stirred at 20-25° C. for 15 minutes. A solution of 4-methylimidazole (17.6 g) and 1-methyl-2-pyrrolidinone (181 g) is slowly added to the mixture over 30 minutes, maintaining the batch temperature between 20-25° C. After the addition, the mixture is stirred at 20-25° C. for 2 hours. A solution of 3-bromo-5-fluorobenzotrifluoride (XXV) (40 g) and 1-methyl-2-pyrrolidinone (76 g) is slowly added into the mixture over 10 minutes, maintaining the batch temperature between 20-25° C. After the addition, the mixture is stirred at 20-25° C. for 16 hours.

Water (720 g) is slowly added to the mixture over 3 hours, maintaining the batch temperature between 20-25° C. After the addition, the mixture is stirred at 20-25° C. for 1 hour. Any solid is isolated by filtration, rinsed with a solution of 1-methyl-2-pyrrolidinone (41 g) and water (100 g), and then rinsed with water (100 g). The solid is air-dried in the funnel for 1 hour.

A 2 L, 4-neck, round-bottom flask under nitrogen purge is charged with the solid (~50 g) and ethyl acetate (361 g). The mixture is stirred for 5 minutes at 20-25° C. until a solution is obtained. The solution is washed with water (2×100 g). The organic layer is distilled at 100 mm Hg at 40° C. until a residual volume of 100 mL is reached. Heptane (342 g) is added, and the mixture is distilled at 400 mm Hg at 60° C. until a residual volume of 300 mL is reached. This operation is repeated one more time. The residue is cooled from 55° C. to 20° C. over 5 hours, and stirred for an additional 1 hour at 20° C. The mixture is cooled to 5° C. over 1 hour and stirred for an additional 1 hour at 5° C. Any solid is isolated by filtration and rinsed with cold (5° C.) heptane (68 g). The cake is dried at 5 mm Hg/20-25° C. for 4 hours to yield (XXVI) (24.3 g, 48% yield) as a white solid:

$^1$H NMR 300 MHz, DMSO-d$_6$), δ 8.45 (s, 1H), 8.30 (s, 1H), 8.10 (s, 1H), 7.90 (s, 1H), 7.70 (s, 1H), 2.10 (s, 3H).

EXAMPLE 2

5-(4-Methyl-1H-imidazol-1-yl)-3-(trifluoromethyl)-benzenamine (I)

Scheme 13

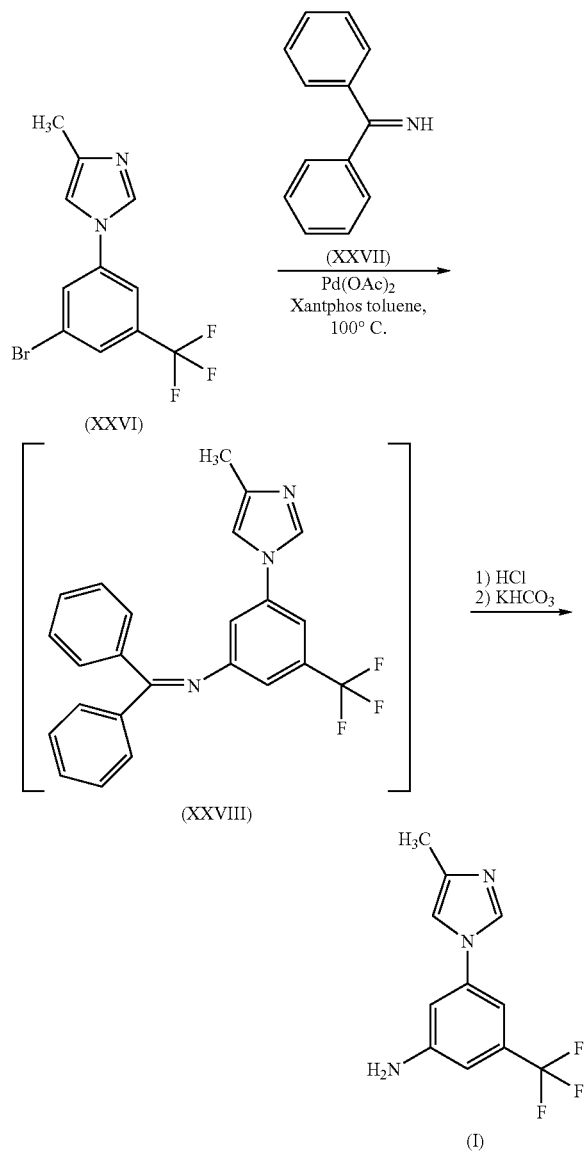

A 1 L, 4-neck, round-bottom flask, equipped with a mechanical stirrer, a digital thermometer, heating/cooling capacity, a condenser, an addition funnel and a nitrogen inlet/outlet, is charged with toluene (400 mL) under nitrogen purge. The toluene is heated to 113° C., stirred at this temperature for an additional 1 hour, and cooled to 20-25° C. In a separate 1 L flask equipped with a mechanical stirrer, a digital thermometer, heating/cooling capacity, a condenser, an addition funnel and a nitrogen inlet/outlet is charged with (XXVI) (40 g) and the above degassed toluene (240 mL). The suspension is stirred at 20-25° C. for 5 minutes to obtain a clear solution. Sodium t-butoxide (17.6 g) is added to the mixture, followed by a mixture of 4,5-bis(diphenylphosphino)-9,9-dimethylxanthene (1.5 g), palladium (II) acetate (0.3 g), and degassed toluene (120 mL). A solution of benzophenone imine (XXVII) (26.4 g) and degassed toluene (40 mL) is added. The mixture is heated to 97-103° C. and stirred at this temperature for an additional 3 hours. The mixture is cooled to 60° C. Water (200 mL) is added, while maintaining the temperature at 20-40° C. The organic layer is separated.

A slurry of PICA P1400 activated carbon (8 g) in toluene (80 mL) is added to the organic layer. The resulting slurry is heated to 80-85° C. and stirred for an additional 5 hours the mixture is cooled to 20-25° C. and stirred at 20-25° C. for an additional 1 hour. The mixture is filtered through a pad of Hyflo Super Celite (4 g) and rinsed with toluene (160 mL). The same operations in the above paragraph are repeated one more time. The organic solution is concentrated under vacuum until a volume of 200 mL is reached. Acetone (600 mL) is added and the mixture is heated to 35±3° C. Concentrated (37%) hydrochloric acid (14.2 g) is added, while maintaining the temperature below 40° C. The mixture is stirred at 35-40° C. for 2 hours, cooled to 20-25° C., and stirred for an additional 1 hour. Any solid is collected by filtration, rinsed with acetone (40 mL), and dried at 60° C./5 mm Hg for 8 hours to yield (I) HCl salt (31.2 g) as a white solid. The solid is dissolved into methanol (312 mL) at 40° C. A solution of potassium hydrogen carbonate (15.7 g) and water (936 mL) is added over 2 hours, while maintaining the batch temperature at 30° C. The mixture is cooled to 20° C. and stirred at 20° C. for an additional 1 hour. Any solid is collected by filtration, rinsed with water (80 g), and dried at 60-75° C./5 mm Hg for 16 hours to yield (I) (23.5 g, 74% yield) as a white solid:

$^1$H NMR (300 MHz, DMSO-$d_6$, $\delta$ 8.05 (s, 1H), 7.40 (s, 1H), 7.00 (s, 1H), 6.95 (s, 1H), 6.85 (s, 1H), 5.90 (s, 2H), 2.15 (s, 3H).

EXAMPLE 3

Preparation of 2-Bromo-5-fluoro-1-nitro-3-trifluoromethyl-benzene, compound of formula (XVIII)

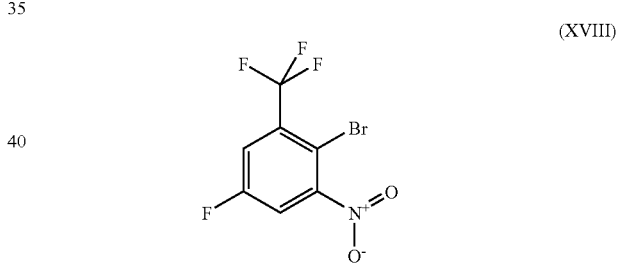

2-Bromo-5-fluoro-benzotrifluoride (XVII) (50 g, purchased from ABCR, F01421) is dissolved in 750 mL of dichloromethane. Potassium-nitrate (60.54 g) is added under stirring, followed by slow addition of sulfuric acid (587.3 g, 20% SO$_3$, Riedel de Haen 30736). The temperature of the reaction mixture is kept at 25-30° C. by gentle cooling during the addition of the sulfuric acid. The reaction mixture is stirred for additional 25 hours at room temperature, after which time an IPC indicated >97% conversion. For work-up, the layers are separated and the acid layer is extracted by stirring with dichloromethane (2×300 mL). The dichloromethane phases are combined and washed sequentially with 1,000 mL of saturated aqueous NaHCO$_3$ solution, 1,000 mL of aqueous sulfamic acid solution (5% m/m), 1,000 mL of saturated aqueous NaHCO$_3$ solution and 1,000 mL of water. The dichloromethane solution is dried on anhydrous MgSO$_4$ and the solvent is evaporated under reduced pressure to obtain 2-bromo-5-fluoro-1-nitro-3-trifluoromethyl-benzene (XVIII) as a yellow liquid. GC-MS: m/z: 287, 268, 257, 241, 229. These mass peaks are accompanied by the corresponding isotope peaks characteristic for bromine containing compounds. IR (film): 3101, 1618, 1591, 1554, 1454, 1423, 1365, 1319, 1232, 1186, 1153, 1113, 883 cm$^{-1}$.

$^1$H-NMR (400 MHz, DMSO-d$_6$): δ 8.13 (dd, J=8.5 and J=2.5 Hz), 8.42 (dd, J=7.6 and J=3.0 Hz).

EXAMPLE 4

3-Fluoro-5-trifluoromethyl-phenylamine, compound of formula (XIX)

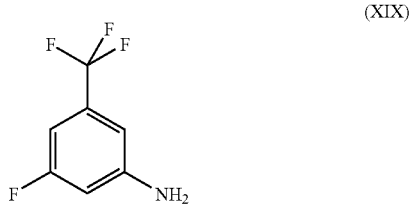

(XIX)

2-Bromo-5-fluoro-1-nitro-3-trifluoromethyl-benzene (XVIII) (55.5 g) is dissolved in 500 mL of ethanol. Triethylamine (19.63 g) and palladium on charcoal (6 g, Pd/C 10%, Engelhard 4505) are added and the mixture is subjected to hydrogenation at 20-25° C. After 20 hours reaction time, the consumption of hydrogen had ceased. The hydrogen pressure is released and the solution is separated from the catalyst by filtration on Cellflock. The filter residue comprising the catalyst is washed with ethanol (2×100 mL). The filtrate and wash fractions are combined and the solution thus obtained is concentrated at 45° C. under reduced pressure to a final volume of ca. 400 mL. Toluene (400 mL) is added and the resulting solution is concentrated to a final volume of ca. 250 mL to obtain a suspension. The precipitate is removed by filtration and the filter cake is washed with toluene (2×100 mL). The solution is concentrated again to a final volume of 200 mL and the formed precipitate is removed again by filtration. The filter cake is washed with toluene (3×50 mL). The process of dilution with toluene, concentration and filtration is repeated until no substantial precipitation occurred in the toluene solution. Finally, the solvent is evaporated at 45-50° C. under reduced pressure and the residue is dried in vacuo at 45° C. to obtain 3-fluoro-5-trifluoromethyl-phenylamine as a yellow oil. GC-MS: m/z: 179, 160, 151, 140, 132. The product is identical in GC and HPLC to a sample of 3-amino-5-fluoro-benzotrifluoride, purchased from ABCR (ABCR F01075). Also the NMR spectra are identical to the sample purchased from ABCR.

EXAMPLE 5

3-(4-Methyl-imidazol-1-yl)-5-trifluoromethyl-phenylamine (I)

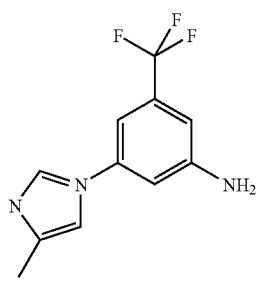

(I)

Sodium hydride (12.18 g, 55-65% m/m, Fluka 71620) is suspended in tetrahydrofuran (60 mL) and a solution of 4-methylimidazole (24.5 g) in tetrahydrofuran (65 mL) is slowly added to the stirred suspension at 20-25° C. Gentle cooling is necessary to maintain the temperature at 20-25° C. during the addition. After completion of the addition, the reaction mixture is stirred for additional 15 minutes at 20-25° C., until gas evolution had ceased. A solution of 3-fluoro-5-trifluoromethyl-phenylamine (XIX) (25 g) in 1-methyl-2-pyrrolidone (125 mL) is added slowly to the reaction mixture and the mixture is stirred for additional 15 minutes at 20-25° C. Then, the reaction mixture is heated at an oil bath temperature of 100° C. to distill off the volatile solvent (tetrahydrofuran). Finally, the temperature is raised to 165° C. (oil bath) and the reaction mixture is stirred for 22 hours at this temperature. For work up, the reaction mixture is poured onto water (500 mL) and the water phase is extracted with t-butyl methyl ether (2×500 mL). The t-butyl methyl ether phases are combined and are extracted with water (2×500 mL). The organic layer is dried on anhydrous magnesium sulfate (19 g) and the solvent is evaporated at 45° C. under reduced pressure to obtain crude 3-(4-methyl-imidazol-1-yl)-5-trifluoromethyl-phenylamine as a yellowish solid. The crude product is contaminated with at least 1 regioisomer. The crude product is dissolved in toluene (93.4 g) at 80-90° C. and the solution is allowed to cool down to room temperature. Crystallization occurred at ca. 35-40° C. The suspension is stirred for additional 2 hours at room temperature and the product is isolated by filtration. The filter cake is washed with ice-cold toluene (25 mL) and dried in vacuo at 50° C. to obtain pure 5-(4-methyl-imidazol-1-yl)-3-trifluoromethyl-phenylamine (I). GC-MS: m/z 241, 222, 213, 200, 186, 172, 160.

$^1$H-NMR (400 MHz, DMSO-d$_6$): δ 2.15 (3H), 5.85 (2H), 6.79 (1H), 6.91 (1H), 6.95 (1H), 7.34 (1H), 8.04 (1H).

In particular, as described above, the bromine substituent can selectively be removed by reduction to obtain 3-fluoro-5-nitro-benzotrifluoride (XIII). The synthesis of compound (I) from compound (XIII) is described in Scheme 6 above.

Scheme 15

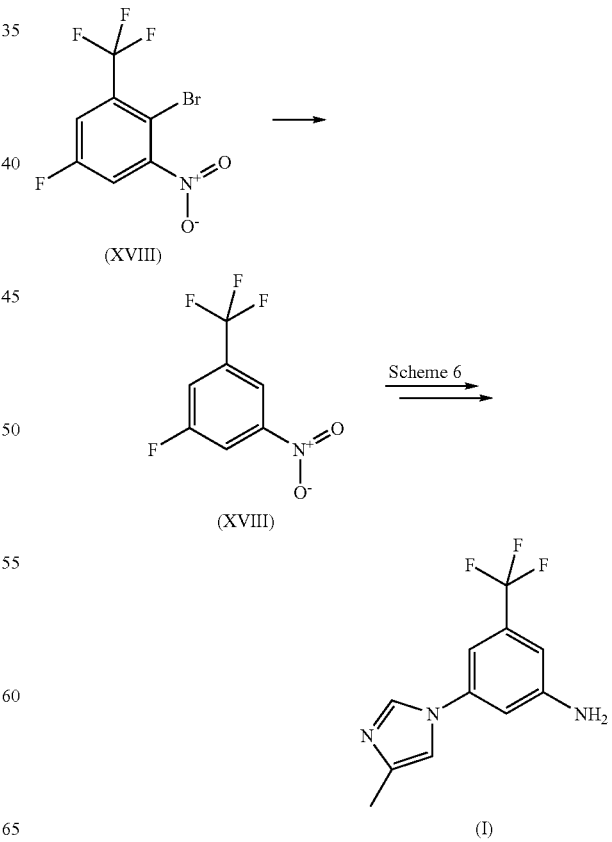

EXAMPLE 6

5-(4-Methyl-imidazol-1-yl)-3-trifluoromethyl-benzonitrile (XXII)

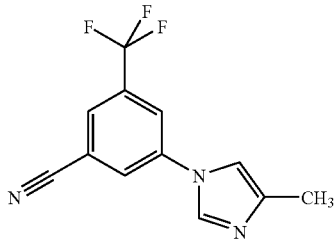

(XXII)

A solution of 4-methyl-1H-imidazole (1.98 g, 24.11 mmol) in N-methylpyrrolidinone (NMP) (18 mL) is added to a solution of sodium hydride (0.82 g, 60%, 20.5 mmol) in NMP (18 mL) at 20-25° C. under an atmosphere of nitrogen. The mixture is stirred for 1 hour, before a solution of 3-fluoro-5-trifluoromethyl benzonitrile (XXI) (3.2 g, 16.4 mmol) in NMP (8 mL) is added. The reaction mixture is stirred for 2 hours at 20-25° C. and then water (120 mL) is added within 20 minutes and the resulting suspension is stirred for 16 hours.

The precipitate is filtered, washed with water (20 mL), dissolved in ethyl acetate (70 mL) and the organic layer is washed with water (50 mL). The aqueous phase is extracted with ethyl acetate (2×40 mL) and the combined organic layers are reduced to a volume of 50 mL in vacuo. Following a heptane (68 mL) addition the crystallization of the product occurs. The suspension is cooled to 0° C. and stirred for 2 hours before being filtered. The filter cake is washed with cold heptane (2×15 mL) and dried in vacuo to give 3.1 g of the title compound (75.3%) as white crystals (73.7% area by HPLC).

EXAMPLE 7

3-(4-Methyl-imidazol-1-yl)-5-trifluoromethyl-benzamide (XXIII)

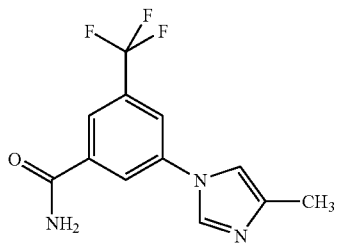

(XXIII)

A solution of 5-(4-methyl-imidazol-1-yl)-3-trifluoromethyl-benzonitrile (3.5 g, 13.93 mmol) in NMP (28 mL) is treated with aqueous ammonia (9.8 mL, 25%) and aqueous hydrogen peroxide (3.5 mL, 30%). The resulting mixture is stirred for 1 hour at 20-25° C. and then poured into chilled water (420 mL). The resulting suspension is filtered and the filter cake is washed with water (50 mL), and dried in vacuo at 50° C. to give 3.2 g of the title compound (XXIII) (85.4%) as white crystals (98% area by HPLC).

EXAMPLE 8

5-(4-Methyl-1H-imidazol-1-yl)-3-trifluoromethyl-phenylamine (I)

A solution of 3-(4-methyl-imidazol-1-yl)-5-trifluoromethyl-benzamide (XXIII) (1 g, 3.71 mmol) in t-butanol (10 mL) and water (3.8 mL) is treated with aqueous solutions of sodium hypochlorite (3.7 mL, 9%) and sodium hydroxide (1.5 mL, 30%). The reaction mixture is stirred for 16 hours at 60° C. and followed by an addition of a solution of sodium hydrogensulfite (2 mL, 10%). The organic phases is separated and treated with toluene (5 mL) and water (2.5 mL) and then aqueous HCl (2 M, 5 mL) is added. The resulting suspension is stirred for 1.5 hours, cooled to 0° C. and filtered. The filter cake is washed with toluene (3 mL) and dried in vacuo to give 0.39 g of the hydrochloride of the title compound (43.2%) as orange crystals, (99.7% area by HPLC). For liberation of the aniline the product is treated with an aqueous solution of potassium hydrogencarbonate (2.2 mL, 5%) in ethano (1 mL) at 45° C. for 0.5 hour. The reaction mixture is then to cooled to 0° C. within 1 hour and stirred for 2 hours. The product is isolated by filtration, washed with ethanol (2×0.75 mL) and dried in vacuo at 50° C. to give 0.27 g of the title compound (I) (32.8%) as off-white crystals (>99.9% area by HPLC).

EXAMPLE 9

5-(4-Methyl-1H-imidazol-1-yl)-3-trifluoromethyl-phenylamine (I)

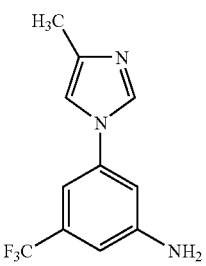

(I)

To a single neck flask fitted with a condenser are added CuI (89.5 mg, 0.47 mmol), cyclohexanediamine (107.3 mg, 0.94 mmol) and diglyme (10 mL). The mixture is stirred for 10 minutes at ambient temperature. To the purple heterogeneous mixture, 3-bromo-5-trifluoromethyl-phenylamine (XVI) (1.13 g, 4.7 mmol), 4-methyl-1H-imidazole (0.77 g, 9.4 mmol) and $Cs_2CO_3$ (1.53 g, 4.7 mmol) are added. The mixture is heated at 150° C. and stirred for an additional 24 hours. The mixture is cooled to 25° C. and purified by column chromatography (silica gel; EtOAc/MeOH 95:5) to afford (I) as the major product (840 mg).

EXAMPLE 10

4-Methyl-1-(3-nitro-5-trifluoromethyl-phenyl)-1H-imidazole (IX) (by catalyzed coupling)

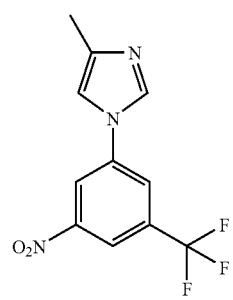

(IX)

To a stirred suspension of 1-bromo-3-nitro-5-trifluoromethyl-benzene (4.05 g, 15 mmol), 4-methyl-1H-imidazole (2.01 g, 24 mmol, 98%), and potassium carbonate (3.73 g, 27 mmol) in N,N-dimethylformamide (10 mL) are added ethylenediamine (0.141 mL, 2.1 mmol) and copper(I) iodide (0.204 g, 1.05 mmol). The vigorously stirred mixture is heated to 110° C. for 23 hours. After that, most of the 1-bromo-3-nitro-5-trifluoromethyl-benzene is converted, and the suspension is allowed to cool down to room temperature. The mixture is diluted with tert-butyl methyl ether (30 mL) and 5% aqueous NaCl solution (30 mL) and isopropyl acetate (15 mL) are added. The aqueous layer is separated and extracted with a mixture of tert-butyl methyl ether (10 mL) and isopropyl acetate (5 mL). The organic layers are combined and filtered. The filtrate is washed with water (10 mL), treated for 5 minutes with ethylenediamine (0.303 mL), washed with water (10 mL), 5% aqueous sodium metabisulfite solution (10 mL) and water (10 mL) before it is treated with activated carbon (1.2 g) at room temperature for 1 hour. The suspension is filtered using filter aid, and the filtrate is evaporated to dryness under reduced pressure to give a clear, red-brown oil which solidifies upon standing at room temperature. The obtained solid is purified by column chromatography on silica gel eluting with a 4:5 mixture of ethyl acetate and hexane (in the presence of 0.5 volume % of triethylamine) to afford mainly 4-methyl-1-(3-nitro-5-trifluoromethyl-phenyl)-1H-imidazole as a pale yellow solid. Yield: 21.1% (HPLC purity: 96.7 area %) Melting point: 118-119° C.

EXAMPLE 11

3-(4-Methyl-imidazol-1-yl)-5-trifluoromethyl-phenylamine (I)

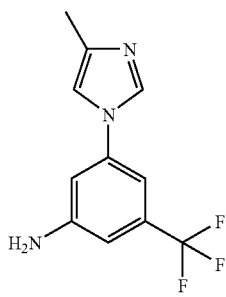

(I)

In an autoclave a suspension of 5% palladium on activated carbon (0.6 g) in 94% aqueous ethanol (200 mL) is pre-hydrogenated. After that, 4-methyl-1-(3-nitro-5-trifluoromethyl-phenyl)-1H-imidazole (6.0 g, 22.1 mmol) is added, and the mixture is hydrogenated at 70° C. and 4 bar pressure for 3 hours. Thereafter, most of the starting material is converted. The suspension is filtered over filter aid. The obtained filtrate is slowly added to water (250 mL) of 0-5° C. The resulting mixture is concentrated to a weight of 270 g, stirred, cooled to 0° C. and further stirred for almost 3 hours. The formed solid is filtered, washed with water (20 mL) and dried at 50° C. under reduced pressure to afford 3-(4-methyl-imidazol-1-yl)-5-trifluoromethyl-phenylamine as an off-white solid. Yield: 85.8% (HPLC purity: 94 area %), Melting range: 123-124° C.

EXAMPLE 12

4-Methyl-1-(3-nitro-5-trifluoromethyl-phenyl)-1H-imidazole methanesulfonic acid salt (XXIX)

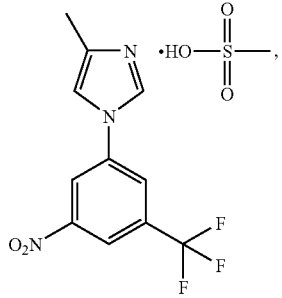

(XXIX)

Crude 4-methyl-1-(3-nitro-5-trifluoromethyl-phenyl)-1H-imidazole (IX) (1.85 g, 6 mmol, 88 area % purity in HPLC) is dissolved in ethyl acetate (6 mL) at about 50° C. To the stirred resulting black solution is slowly added methanesulfonic acid (0.397 mL, 6 mmol) at about 50° C. At the end of the addition a bright solid starts to precipitate. The mixture is allowed to slowly cool down to room temperature and is further stirred at about 5° C. for 75 minutes. The solid formed is filtered, washed with ethyl acetate (4 mL) and dried at room temperature and reduced pressure. A suspension of the obtained material in 2-propanol (5 mL) is stirred at 50° C. for 90 minutes, is allowed to cool down to room temperature, stirred for 1 hour and at 0-5° C. for another hour. The solid formed is filtered, washed with cold 2-propanol (5 mL) and dried at room temperature and reduced pressure to afford 4-methyl-1-(3-nitro-5-trifluoromethyl-phenyl)-1H-imidazole methanesulfonic acid salt as a beige solid. Yield: 54.1% (HPLC purity: 99.5 area %), Melting point: 208-213° C.

EXAMPLE 13

4-Methyl-1-(3-nitro-5-trifluoromethyl-phenyl)-1H-imidazole (IX) (by aromatic substitution)

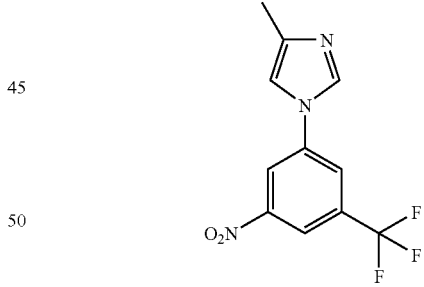

(IX)

4-Methylimidazole (10.5 g, 125.5 mmol) and potassium carbonate (12.0 g, 119.6 mmol) is suspended in N,N-dimethylformamide (80 mL) and stirred at 100° C. for 1 hour. A solution of 1-fluoro-3-nitro-5-trifluoromethyl-benzene (12.5 g, 59.8 mmol) in N,N-dimethylformamide (20 mL) is added over 10 minutes. The mixture is stirred at 108° C. internal temperature for 3 hours. HPLC analysis shows complete consumption of the fluoride starting material. The mixture is cooled down to about 20° C. and water (200 mL) is added over 1 hour. The resulting suspension is filtered to give 17.5 g of wet solid (HPLC: 88.8 area % desired isomer, 8.9 area % undesired isomer/byproduct). A suspension of this material in water (100 mL) is stirred for 1 hour at room-temperature. The solid is filtered, washed with water (100 mL) and dried at 50° C. under reduced pressure to give the crude product. HPLC analysis shows more than 90 area % of the desired product. Re-crystallization: A solution of above crude product (9.5 g) in ethyl acetate (50 mL) is treated for 2 hours at 70° C. with activated carbon (1 g) and filter aid (1 g) and, thereafter, is filtered, and the filtrate is evaporated to dryness to give 11.1 g of a residue. This material is dissolved in ethyl acetate (3.25 g) and heptane (50 mL) under reflux. The solution is seeded at 65° C. with 4-methyl-1-(3-nitro-5-trifluoromethyl-phenyl)-1H-imidazole and allowed to cool down to room temperature over night and afterwards stirred at 0° C. for 3 hours. The solid formed is filtered, washed with heptane (20 mL) and dried at 50° C. under reduced pressure to give 4-methyl-1-(3-nitro-5-trifluoromethyl-phenyl)-1H-imidazole as a solid. Yield overall: 53.3% (HPLC purity: 98.2 area %), Melting point: 117-118° C.

EXAMPLE 14

1-Bromo-3-nitro-5-trifluoromethyl-benzene (XI)

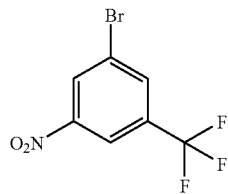

(XI)

To a solution of 1-nitro-3-trifluoromethyl-benzene (41.1 mL, 300 mmol, 97%, purchased from Aldrich) in dichloromethane (240 mL) is added 98% sulfuric acid (45.7 mL, 840 mmol) over 10 minutes. The vigorously stirred resulting biphasic mixture is warmed to 35° C. and 1,3-dibromo-5,5-dimethyl-imidazolidine-2,4-dione (53.1 g in total, 180 mmol) is added in six equal portions over five hours. The mixture is stirred at 35° C. for additional 19 hours. Thereafter, more than 97% of the starting material is converted according to HPLC analysis. The reaction mixture is allowed to cool to room temperature and added over 20 minutes to a stirred 2 M aqueous NaOH solution (210 mL) of 0-5° C. while cooling with an ice-water bath. The internal temperature rises temporarily to about 35° C. The two layers are separated. The aqueous layer is extracted with hexane (3×200 mL). The combined organic layers are washed with water (200 mL), 5% aqueous sodium metabisulfite solution (2×200 mL), 8% aqueous NaHCO$_3$ solution (200 mL) and 10% aqueous NaCl solution (200 mL) and, thereafter, the solvents are evaporated at reduced pressure and 45° C. The obtained liquid is distilled at 0.71 mbar and a bath temperature of 70-80° C. to give 1-bromo-3-nitro-5-trifluoromethyl-benzene as a pale yellow liquid. Yield: 89.6% ($^1$H-NMR purity: about 95%). $^1$H-NMR (400 MHz, CDCl$_3$): 8.11 ppm (m, 1 H), 8.45 ppm (m, 1 H), 8.58-8.59 ppm (m, 1 H). Boiling point: approximately 68° C. at 0.71 mbar.

What is claimed is:

1. A process for preparing 5-(4-methyl-1H-imidazol-1-yl)-3-(trifluoromethyl)-benzenamine (I) comprising reacting 4-methyl-1H-imidazole, or a salt thereof, and a compound of the formula:

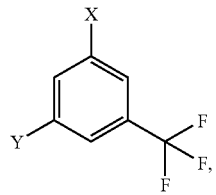

wherein
X is halogen, sulfonate or NO$_2$; and
Y is NH$_2$, NO$_2$ or halogen,
in the presence of a suitable base or a suitable transition metal catalyst or combination thereof, in an appropriate solvent.

2. The process of claim 1,
wherein
Y is NO$_2$; and
X is halogen, sulfonate or NO$_2$, comprising the steps of:
Step a) reacting, using a suitable base in an appropriate solvent, 4-methyl-1H-imidazole, or a salt thereof, with a compound of the formula:

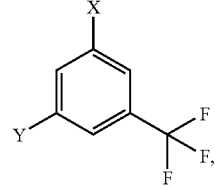

to prepare 4-methyl-1-(3-nitro-5-trifluoromethyl-phenyl)-1H-imidazole; and
step b) reducing the resulting 4-methyl-1-(3-nitro-5-trifluoromethyl-phenyl)-1H-imidazole using a transition metal catalyst in a suitable polar solvent.

3. The process of claim 2,
wherein
Y is NO$_2$; and
X is Br or I, wherein
Step a) comprises the use of a transition metal catalyst and a suitable base in an appropriate solvent; and
Step b) comprises a reduction step using a transition metal catalyst in a suitable polar solvent.

4. The process of claim 2,
wherein
Y is NO$_2$; and
X is F, wherein
Step a) comprises the use of a suitable base in an appropriate solvent at elevated temperature; and
Step b) comprises a reduction step using a transition metal catalyst in a suitable polar solvent.

5. The process of claim 2, wherein Step a) is conducted at about 70° to about 130° C.

6. The process of claim 2, wherein the base is a potassium alkoxide, sodium alkoxide, lithium alkoxide, potassium hydride, sodium hydride, or a carbonate of lithium, sodium, potassium or cesium.

7. The process of claim 2, wherein the solvent used in Step a) is N,N-dimethylformamide, N,N-dimethylacetamide or 1-methyl-2-pyrrolidinone.

8. The process of claim 2, wherein the polar solvent used in Step b) is ethanol.

9. A process for producing 5-(4-methyl-1H-imidazol-1-yl)-3-(trifluoromethyl)-benzenamine (I) comprising reacting 4-methyl-1H-imidazole with 3-bromo-5-trifluoromethyl-phenylamine in an suitable base and an appropriate solvent.

10. A process for preparing 5-(4-methyl-1H-imidazol-1-yl)-3-(trifluoromethyl)-benzenamine (I) comprising the following reaction:

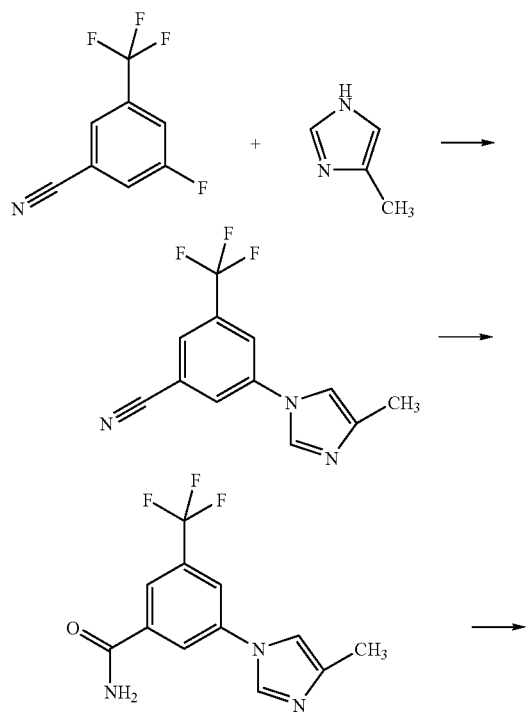

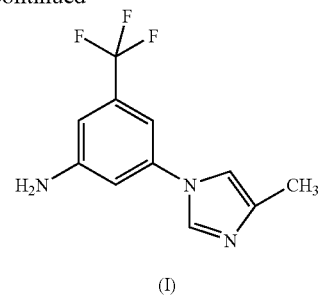

using a suitable base in an appropriate solvent.

11. A process for preparing 5-(4-methyl-1H-imidazol-1-yl)-3-(trifluoromethyl)-benzenamine (I) comprising reacting methyl-1H-imaidazole with 3-fluoro-5-trifluoromethyl-phenylamine in an suitable base and an appropriate solvent.

12. A process according to claim 1, wherein microwave fields are used.

13. A process according to claim 1, wherein a faster heating and cooling cycle is achieved by additional heat exchanger capacity in batch vessels or by using continuous reaction equipment to obtain higher selectivity.

* * * * *